United States Patent [19]

Arima et al.

[11] Patent Number: 5,401,895
[45] Date of Patent: Mar. 28, 1995

[54] PROCESS FOR PREPARING DIVINYLBENZENE

[75] Inventors: Tomiho Arima, Kitakyushu; Toyoki Fujita, Oita; Yasuhiko Ikeda, Oita; Masahiro Mikajiri, Oita, all of Japan

[73] Assignee: Nippon Steel Chemical Co., Ltd., Tokyo, Japan

[21] Appl. No.: 122,960

[22] Filed: Sep. 20, 1993

[30] Foreign Application Priority Data

Sep. 30, 1992 [JP] Japan .................. 4-283523

[51] Int. Cl.6 .................................... C07C 5/333
[52] U.S. Cl. .................... 585/440; 585/441
[58] Field of Search ...................... 585/440, 441

[56] References Cited

U.S. PATENT DOCUMENTS 2,775,629 12/1956 Anderson ............... 585/440
3,515,767 5/1970 Carson .................. 585/441

FOREIGN PATENT DOCUMENTS 0217492 4/1987 European Pat. Off. .
43-29373 12/1943 Japan .................. 585/441
62-45542 2/1987 Japan .

Primary Examiner—Asok Pal
Attorney, Agent, or Firm—Nikaido, Marmelstein, Murray & Oram

[57] ABSTRACT

In the recovery of dehydrogenation oil from the reaction product gas from the vapor-phase catalytic dehydrogenation of diethylbenzene by condensing the gas in a condenser, this invention relates to a process for preparing divinylbenzene by spraying a high-boiling oil or a high-boiling oil and water inside the condenser and letting the oil or the oil and water contact the reaction product gas and the process is capable of dehydrogenating diethylbenzene at high levels of conversion and selectivity without blocking of the condenser and yielding divinylbenzene of high concentration efficiently in a long-term stable continuous operation.

6 Claims, No Drawings

PROCESS FOR PREPARING DIVINYLBENZENE

FIELD OF THE INVENTION AND RELATED ART STATEMENT

This invention relates to a process for preparing divinylbenzene.

Divinylbenzene, on account of its having two double bonds, is useful as crosslinking agent for a variety of resins and is used as raw material for ion exchange resins and as modifier for a variety of resins.

Divinylbenzene can be prepared by the dehydrogenation of diethylbenzene. For example, there is a description in EP 0217492 A1 that the dehydrogenation of para-diethylbenzene with a purity of 93% in the presence of an alkaline dehydrogenation catalyst at a temperature of 620° to 630° C. and at a steam to diethylbenzene ratio (hereinafter referred to as S/D ratio) of 2 to 4 (by weight) occurred at a conversion of approximately 80% to yield approximately 38% by weight of para-divinylbenzene and approximately 30% by weight of para-ethylvinylbenzene. Another description is found in Japan Kokai Tokkyo Koho No. Sho 62-45,542 (1987) that diethylbenzene was dehydrogenated to divinylbenzene at a conversion of approximately 78% with a selectivity (mol) to divinylbenzene of approximately 55% under the conditions where the inlet temperature of the catalyst layer was 620° C., the LHSV based on diethylbenzene was 1 $hr^{-1}$, and the S/D ratio was 3.

Since the dehydrogenation of diethylbenzene such as mentioned above takes place in the vapor phase, it is necessary to recover divinylbenzene by cooling and condensing the dehydrogenation reaction product gas in a condenser. Divinylbenzene, however, is highly reactive and readily undergoes polymerization. When the recovery of divinylbenzene is attempted by cooling and condensing the dehydrogenation reaction product gas, polymers separate out in the condenser and adhere to the heat-transfer surface of the condenser. This has made it difficult to sustain an operation, if undertaken on a commercial scale, stably over a long period of time. The polymers adhering to the heat-transfer surface of the condenser are extremely difficultly soluble in common solvents and, even though formed in traces at any given instant, they gradually accumulate with the passage of time to such an extent as to cause serious troubles, sometimes leading to an interruption of the operation.

To solve the above-mentioned problems, the present inventors made studies on the addition of polymerization inhibitors as a means to suppress the polymerization of divinylbenzene, but were unable to obtain satisfactory results.

With the problems unsolved, the procedure hitherto followed has been to conduct the dehydrogenation of diethylbenzene at a low level of conversion, recover a product gas containing divinylbenzene in low concentration from the reaction system, condense the gas, and raise the concentration of divinylbenzene by distillation even in the cases where the aim is to recover divinylbenzene in high concentration. With a procedure such as this, not only the distillation load is high but also polymers form during the distillation, and there has arisen a need to prevent the formation of such polymers.

OBJECT AND SUMMARY OF THE INVENTION

The present inventors have undertaken extensive studies to solve the problems in the conventional processes. We have found that divinylbenzene tends to polymerize inside the condenser where the reaction product gas from the dehydrogenation of diethylbenzene is cooled and condensed and it is important to prevent the polymerization at this site and also found that the spraying of a high-boiling oil inside the condenser where polymers tend to adhere can prevent the blocking of the condenser and sustain the operation stably over a long period of time and, as a result, it becomes possible to perform the dehydrogenation of diethylbenzene at high levels of conversion and selectivity. We have completed this invention on the basis of the above-mentioned findings.

Accordingly, it is an object of this invention to prepare divinylbenzene from diethylbenzene in high yield.

Another object of this invention is to prevent the polymerization of divinylbenzene as much as possible during the condensation of the reaction product gas from the dehydrogenation of diethylbenzcne and also to enable a stable operation over a long period of time by preventing the adhesion of polymers to the heat-transfer surface of the condenser.

Thus, in the recovery of the dehydrogenation oil from the reaction product gas from the vapor-phase catalytic dehydrogenation of diethylbenzene by the introduction of the gas into a condenser followed by the condensation of the gas there, this invention relates to a process for preparing divinylbenzene which comprises spraying a high-boiling oil inside the condenser and bringing the oil into contact with the reaction product gas.

Furthermore, in the recovery of the dehydrogenation oil from the reaction product gas from the vapor-phase catalytic dehydrogenation of diethylbenzene by the introduction of the gas into a condenser followed by the condensation of the gas there, this invention relates to a process for preparing divinylbenzene which comprises spraying a high-boiling oil and water inside the condenser and bringing said oil and water into contact with the reaction product gas.

This invention will be described in detail below.

The dehydrogenation reaction for the preparation of divinylbenzene from diethylbenzene can be carried out by bringing diethylbenzene together with steam into contact with a dehydrogenation catalyst, for example, iron oxide containing catalyst, in the vapor phase. The process of this invention is effective when the dehydrogenation reaction is carried out at a conversion of 70% or more, preferably 80% to 90%, and particularly so when the selectivity of divinylbenzene in the dehydrogenation reaction is 40% by weight or more. The other conditions for the dehydrogenation reaction may be in the ranges in the public knowledge. It is desirable to conduct the reaction under the conditions where the temperature is 600° to 700° C., the steam/diethylbenzene ratio (by weight) is 5 to 8, and the pressure is normal or reduced.

As the dehydrogenation reaction of diethylbenzene is carried out at 600° to 700° C., the reaction product flowing out of the reactor is gaseous and the reaction product gas is condensed, separated into oil and water, and recovered as dehydrogenation oil. A condenser to be used for the condensation of the reaction product gas is not specified. It can be of any shape and a known heat exchanger may be used as condenser.

According to a knowledge gained by the present inventors, the polymerization is observed to take place extensively at places where gas changes into liquid and it is most important to prevent the polymerization at these places. Hence, the process of this invention effects the condensation of the reaction product gas by spraying a high-boiling oil inside the condenser and letting the oil contact the reaction product gas and quench it. It is preferable to spray the high-boiling oil either immediately before or immediately after the reaction product gas starts to condense and to apply 10 to 100 parts by weight of the high-boiling oil to 100 parts by weight of ingredients with condensing point higher than that of steam in the reaction product gas in order to cause a sufficiently large drop in the temperature of the reaction product gas.

The reaction product gas as used in this invention refers to the gas flowing out of the reactor and the ingredients with condensing point higher than that of steam in the reaction product gas consist of the reaction products derived from the raw material diethylbenzene and the unreacted raw material and contains divinylbenzene, byproducts such as ethylvinylbenzene, unreacted diethylbenzene, and the impurities contained in the raw material. It does not, however, include the steam, hydrogen and the like.

Some polymerization inevitably occurs even if the reaction product gas is quenched by the sprayed high-boiling oil and it is also important to prevent such polymers from adhering to the heat-transfer surface of the condenser. To accomplish this objective, it is effective to let the high-boiling oil flow on the heat-transfer surface at a linear velocity equal to or higher than a certain specified value. In consequence, it is preferable to create the conditions which allow washing of the whole area of the heat-transfer surface with a running stream of the high-boiling oil at all times, although the spraying conditions such as the amount of the high-boiling oil to be sprayed and the rate of spraying vary with the structure of the condenser.

The high-boiling oil to be sprayed inside the condenser has a boiling point higher than that of ethylbenzene, preferably that of divinylbenzene and, to be concrete, it has a boiling point of 140° C. or more, preferably 230° C. or more, and more preferably 250° C. or more. Saturated aromatic hydrocarbons are desirable for such high-boiling oil and their examples are diphenylethane, alkyldiphenylethane, tetraethylbenzene, and aromatic hydrocarbons or fractions mainly consisting of them such as residual oils produced as byproducts in the dealkylation of alkylbenzenes and oils from rapid pyrolysis of coal. They are stable, highly capable of dissolving the polymers formed, and effective for preventing the polymerization. In addition, diethylbenzene, methylnaphthalene, dimethylnaphthalene, ethylnaphthalene, ethylbiphenyl, and methyldiphenyl ether may be cited as high-boiling oils.

It is to be noted that the use of a high-boiling oil with a boiling point roughly equal to that of divinylbenzene makes it difficult to separate the two by distillation.

The high-boiling oil to be sprayed should desirably be at a low temperature, but then there is the possibility of para-divinylbenzene crystallizing out if it is present in high concentration. It is therefore desirable for the oil to be near normal temperature, for example, at 0 to 50° C.

Water may be sprayed simultaneously with the high-boiling oil. Water has a relatively low boiling point, but produces a large cooling effect by its latent heat of vaporization. Effective utilization of water would result if water separated from the condensate containing the dehydrogenation oil obtained by the condensation of the reaction product gas were used for this objective. The amount of water to be sprayed is preferably 100 parts by weight or less per 100 parts, preferably 10 ~ 100 parts by weight of ingredients with condensing point higher than that of steam in the reaction product gas.

The dehydrogenation oil recovered by the condensation contains the unreacted substances, the high-boiling oil, by-products such as polymers, and water in addition to divinylbenzene and it is advantageously subjected to oil-water separation or solid separation and then distilled to refine divinylbenzene. The distillation here is desirably carried out in such a manner as to distil divinylbenzene and leave the high-boiling oil as residue. The separated high-boiling oil may be recycled or utilized as fuel oil.

The distillation is carried out at a reduced pressure in the presence of a polymerization inhibitor in order to prevent polymerization. Moreover, the distillation may be carried out in a device with a single distillation column or in a device with two or more distillation columns. In either case, a fraction boiling lower than divinylbenzene and a fraction boiling higher than divinylbenzene are separated as much as possible from the fraction containing divinylbenzene. Depending upon the reaction conditions, the process of this invention makes it possible to obtain divinylbenzene as a fraction containing 80 to 98% by weight of divinylbenzene, 2 to 20% by weight of ethylvinylbenzene, and 1% by weight or less of saturated compounds. It is desirable to add 100 to 5,000 ppm (by weight) of a polymerization inhibitor to the divinylbenzene fraction immediately after the distillation.

An example of the manufacturing step will be described for the process of this invention.

A diethylbenzene fraction from the ethylbenzene manufacturing process is charged together with steam via a heater into a reactor, where the diethylbenzene is dehydrogenated in contact with a dehydrogenation catalyst. The dehydrogenation reaction product gas is taken out of the reactor and charged into a condenser, where the gas is cooled in the precooling section to such an extent as not to cause condensation and then further cooled in the condensing section to be condensed.

On the other hand, the high-boiling oil is cooled to near normal temperature, sprayed into the condenser of the dehydrogenation reaction product gas, and allowed to contact the reaction product gas flowing from the precooling section to the condensing section.

The dehydrogenation oil obtained in the condenser is drawn and separated from water and the oil is charged into a distillation column to separate a fraction containing divinylbenzene, ethylvinylbenzene, and the like from the column top or from the upper portion of the column and a high-boiling fraction from the column bottom or the lower portion of the column.

The fraction containing divinylbenzene is further distilled, as needed, to yield divinylbenzene of high concentration.

The process of this invention is capable of producing divinylbenzene of high concentration effectively in a stable continuous operation over a long period of time as no blocking of the condenser occurs even when the dehydrogenation of diethylbenzene is carried out at high levels of conversion and selectivity.

DETAILED DESCRIPTION OF THE PREFERRED EMBODIMENTS

The process of this invent ion will be described in detail with reference to the accompanying example and comparative example.

Example 1

The reaction product gas from the dehydrogenation of diethylbenzene (divinylbenzene 45%, ethylvinylbenzene 25%) flowing out of the reactor at 600° C. was charged into the condenser as described in the above-mentioned example of the manufacturing step.

On the other hand, in the ethylbenzene manufacturing process, the ethylation reaction products obtained by the ethylation of benzene with ethylene were distilled, a fraction containing compounds up to ethylbenzene was recovered, the remaining polyethylbenzene fraction was distilled to recover diethylbenzene and a high-boiling oil mainly consisting of diphenylethane and ethyldiphenylethane (composition; diphenylethane 28%, ethyldiphenylethane 46%), and the high-boiling oil was used as the oil to be sprayed inside the condenser for the dehydrogenation reaction product gas. The amount of the high-boiling oil to be sprayed was controlled at 20 parts by weight per 100 parts by weight of ingredients with condensing point higher than that of steam in the reaction product gas to be condensed in unit time inside the condenser. In this example, no blocking of the condenser by polymers occurred in a continuous operation for 3 months.

The dehydrogenation oil recovered in the condenser was separated from water and distilled at a reduced pressure to yield a fraction containing 81.5% by weight of divinylbenzene, 18.1% by weight of ethylvinylbenzene, and 0.4% or less of others. In carrying out the distillation, a polymerization inhibitor was added to prevent the blocking of the distillation column.

Moreover, when 15 parts by weight of the high-boiling oil and 15 parts by weight of water were used to be sprayed, no blocking of the condenser by polymers also occurred in a continuous operation.

Comparative Example 1

When divinylbenzene was prepared under the same conditions as in Example 1 excepting the spraying of the high-boiling oil, the condenser was blocked in a week or so to make the continued operation impossible thereafter.

What is claimed is:

1. A process for preparing divinylbenzene, comprising:
   dehydrogenating a reaction gas comprising diethylbenzene to form a reaction product gas comprising divinylbenzene;
   introducing said reaction product gas into a condenser;
   spraying a high-boiling oil inside said condenser such that said high-boiling oil contacts said reaction product gas, wherein said high-boiling oil has a boiling point higher than that of divinylbenzene; and
   condensing said reaction product gas.

2. A process for preparing divinylbenzene described in claim 1 wherein said high-boiling oil has a boiling point of 230° C. or more.

3. A process for preparing divinylbenzene described in claim 1 wherein said high-boiling oil in the range from 10 to 100 parts by weight is sprayed per 100 parts by weight of ingredients with condensing point higher than that of steam in said reaction product gas.

4. A process for preparing divinylbenzene, comprising:
   dehydrogenating a reaction gas comprising diethylbenzene to form a reaction product gas comprising divinylbenzene;
   introducing said reaction product gas into a condenser;
   spraying a high-boiling oil and water inside said condenser such that said high-boiling oil and water contacts said reaction product gas, wherein said high-boiling oil has a boiling point higher than that of divinylbenzene; and
   condensing said reaction product gas.

5. A process for preparing divinylbenzene described in claim 4 wherein said high-boiling oil has a boiling point of 230° C. or more.

6. A process for preparing divinylbenzene described in claim 4 wherein said high-boiling oil in the range from 10 to 100 parts by weight and said water from 10 to 100 parts by weight are sprayed per 100 parts by weight of ingredients with condensing point higher than that of steam in said reaction product gas.

* * * * *